United States Patent [19]
Mueller

[11] Patent Number: 4,801,297
[45] Date of Patent: Jan. 31, 1989

[54] CATHETER HAVING SLIT TIP
[75] Inventor: Richard L. Mueller, Athens, Tex.
[73] Assignee: Edward Weck Incorporated, Princeton, N.J.
[21] Appl. No.: 616,036
[22] Filed: Jun. 1, 1984
[51] Int. Cl.[4] .......................................... A61M 25/00
[52] U.S. Cl. .................................. 604/280; 604/264; 604/247
[58] Field of Search ................ 604/93, 118, 173, 244, 604/257, 258, 264, 280, 105, 43, 27, 39, 247

[56] References Cited

U.S. PATENT DOCUMENTS

| | | | |
|---|---|---|---|
| 634,363 | 10/1899 | Morrison | 604/280 |
| 1,103,967 | 7/1914 | Hughes | 604/264 |
| 1,806,517 | 5/1931 | Bellows | 604/280 |
| 1,852,427 | 4/1932 | Lopatin | 604/39 |
| 3,020,913 | 2/1962 | Heyer | 604/247 |
| 3,828,767 | 8/1974 | Spiroff | 128/658 |
| 3,888,249 | 6/1975 | Spencer | 604/247 |
| 4,282,876 | 8/1981 | Flynn | 128/658 |
| 4,345,594 | 8/1982 | Bisera et al. | 604/118 |
| 4,385,635 | 5/1983 | Ruiz | 604/280 |
| 4,431,426 | 2/1984 | Groshong et al. | 604/280 |
| 4,445,897 | 5/1984 | Ekbladh et al. | 604/280 |
| 4,531,943 | 7/1985 | Van Tassel et al. | 128/658 |

Primary Examiner—C. Fred Rosenbaum
Assistant Examiner—Gene B. Kartchner
Attorney, Agent, or Firm—Lawrence S. Levinson; Robert E. Lee, Jr.

[57] ABSTRACT

The present catheter employee a series of axial slits adjacent to its tip. The slits act to increase the flexibility of the catheter adjacent the tip thereby providing pressure relief in the event of blockage of the lumen at the tip. In addition, by forming the slits as slots, i.e. by removing material from the slits, it is possible to provide a catheter having flow through the sides adjacent to the tip for any desired purpose.

6 Claims, 1 Drawing Sheet

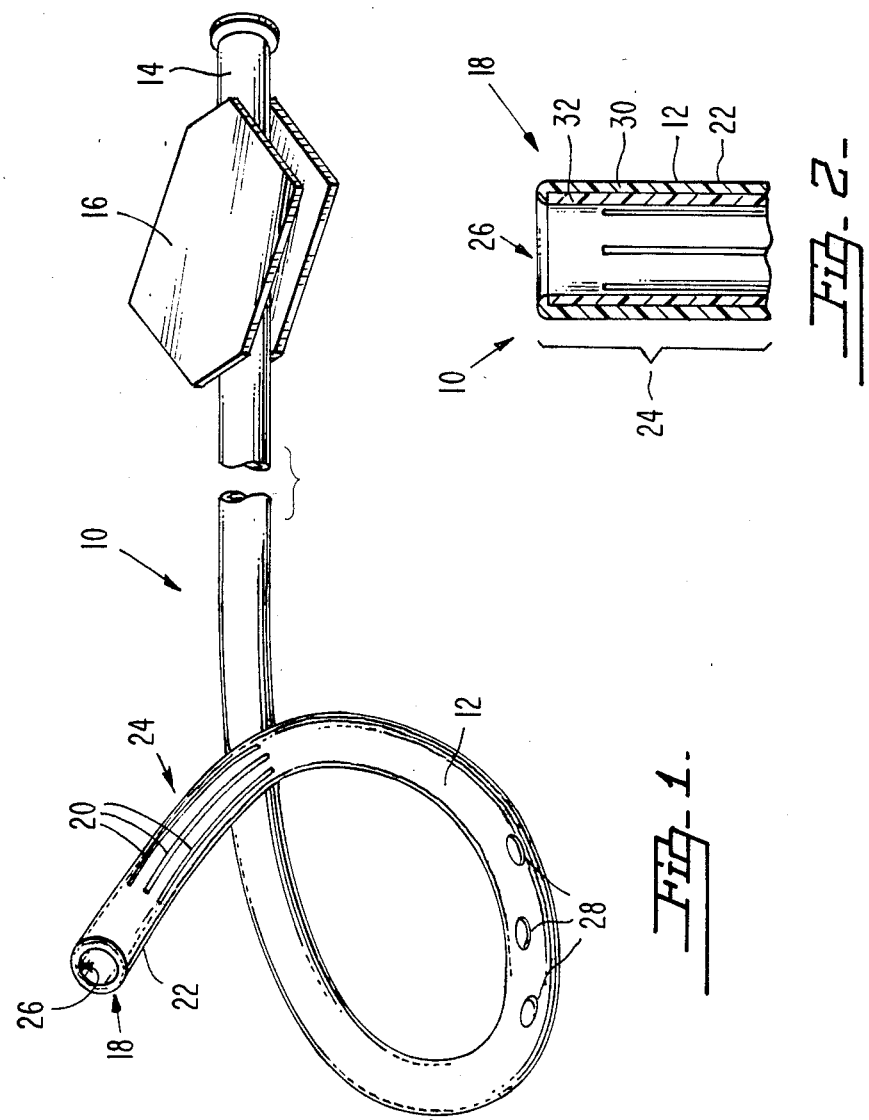

CATHETER HAVING SLIT TIP

BACKGROUND OF THE INVENTION

The present invention relates to catheter designs.

Catheters are used in medical applications to introduce fluids into the body. A variety of catheter designs have been used and are well-known. Typically, catheters are flexible, tube-like structures having a single opening called a lumen. Multiple lumen catheters are also known.

Various designs have been used heretofore to provide a soft tip on catheters in order to help prevent the catheter from puncturing a vessel during vascular insertion. Typically, a soft material is bonded onto the tip of a catheter by some suitable method, i.e. using an adhesive or an ultrasonic bond. A soft tip can also be made part of the catheter by an insertion molding process or by a tapered co-extrusion process. Problems with the soft-tipped catheters heretofore known involve the risk that the soft tip, being a separate part, would fall off. That is particularly important in applications where the tip might be subjected to high fluid pressure. As is well known, if a tip falls off a catheter, causing arterial blockage, extensive surgery is required to retrieve the tip.

SUMMARY OF THE INVENTION

An improved catheter is described. The catheter is of the type having an elongated tube which has an exterior wall defining at least one lumen formed therein. The tube terminates in a tip which has at least one opening in it. In the case of a multi-lumen catheter, there may be more than one opening at the tip, or the different lumens may terminate in side holes in the manner generally known in the art. The improvement in the present invention is that there is at least one slit formed through the wall of the catheter tube adjacent the tip.

BRIEF DESCRIPTION OF THE DRAWING

In the Drawing:

FIG. 1 is a perspective view of the preferred embodiment of the present invention: and FIG. 2 is a cross-sectional view showing the end portion of the catheter of FIG. 1.

DETAILED DESCRIPTION OF THE PREFERRED EMBODIMENT

Referring generally to FIG. 1, the catheter 10 of the present invention is shown. The catheter 10 is comprised of an elongated tube 12 which terminates at one end in a connecting fitting 14 of a type well-known in the art. For example, a Luer lock fitting 14 is used in the preferred embodiment of the invention. Typically, there is a handle area 16 provided in order to grasp the catheter 10 in order to attach the fitting 14. At the opposed end of the catheter 10, there is a tip 18.

As shown, the edges of the tip 18 are rounded and are made of a softer material than the internal portions of the tube 12 (See FIG. 2). The purpose of providing the soft rounded tip 18 is to reduce the risk of arterial wall damage. In addition, the catheter 10 of the present invention employs a series of elongated axial slits 20 which are cut through the side wall 22 of the catheter 10. The purpose of the axial slits 20 is to soften the tip region 24 enabling the catheter 10 to bend very easily within the artery thereby substantially reducing the risk of arterial wall puncture and damage. The slits 20 are cut into the original tubing extrusion, so no secondary bonding process is employed to attach the soft tip region 24 to the catheter 10. This is particularly important in any application in which the tip 18 is subjected to high fluid pressure, as such fluid pressure could blow off a bonded type tip of the type heretofore known.

In addition to offering structural integrity, due to the absence of a secondary bonding operation, the elongated axial slits 20 act as a safety valve at the tip 18. This safety valve function is extremely important when the catheter 10 is inserted into a location where the opening 26 at the end of the tip 18 is blocked against an arterial wall, resulting in complete occlusion of the end opening 26. As is known, a catheter 10 in this condition can blow a hole in the arterial wall as external pressure is applied to fluids within the catheter 10. Under these conditions, side holes 28, of the type heretofore used in catheters, provide a limited safety mechanism. However, as the side holes 28 are typically one to two inches back from the tip 18, and as they typically have a fixed size, the speed at which they can act as a pressure release is fixed. The axial slit design of the catheter 10 of the present invention, however, causes any deflection of the tip region 24 to open some of the slits 20, thereby providing pressure release very close to the tip 18. In accordance with the present invention, the slits 20 begin approximately ⅛" back from the tip 18. Accordingly, the pressure release function is provided close to the tip 18 and is superior to the safety provision provided by side holes of the type heretofore known.

An additional advantage of the axial slits 20 in the tip region 24 relates to enhanced flow rate and dispersion. For example, on high pressure angiographic imaging, the flow rate and dispersion become critical factors. Accordingly, the medical industry has generally used side holes to increase flow rate, increase flow dispersion, and to prevent "tip whip", i.e., to prevent the tip 18 from moving in reaction to the flow out of it. With the slit tip design of the present catheter 10, either with or without side holes 28, improved flow and flow dispersion are provided, while catheter tip whip is reduced.

In accordance with the present invention, the tip 18 may be tapered, and it may have a softer exterior material 30 of a co-extrusion which is rolled around and over the rigid inner material 32 thereby removing the abrasive edge normally present due to the rigid inner material 32 (See FIG. 2). The axial slit design may also be used without a co-extrusion material. For example, single material extrusions such as nylon, urethane, or teflon will function well. In those situations where increased flow is desired, the slits 20 may be expanded into slots, i.e. rather than just cutting an elongated slit 20 through the side wall 22 of the catheter 10 without removing material, material may actually be removed in order to form slots for increased flow. In addition, the number of slits 20 may be changed as may be the length of the slits 20 and the distance from the tip 18 to the start of the slits 20.

The present invention has been found to be well suited to small diameter, high pressure applications, such as angiographic catheters, digital subtraction angiography catheters, and other vascular applications. As will be recognized by those of ordinary skill in the art, the number of slits 20, their length and their widths, i.e. slots, and their distance from the catheter tip 18 will vary with the particular application for which the catheter is to be used without departing from the present invention, i.e., different French sizes, materials, and degrees of softness may be provided. Similarly, the axial slit design can be used with multi-lumen catheters without departing from the present invention. In such applications, the various lumens can each have from zero to any desired number of slits. Accordingly, variations in these parameters are considered to be within the scope of the present invention.

I claim:

1. An improved catheter of the type having an elongated tube having an exterior wall defining at least one lumen formed therein, said tube terminating in a tip having at least one opening to said at least one lumen, wherein the improvement comprises a soft tip which is able to easily bend within a patient's vessel thereby reducing the probability of vessel wall injury, said soft tip being comprised of at least one slit formed through said wall of said tube adjacent said tip, whereby said at least one slit will function as both a pressure release to allow fluid under high pressure to escape from said catheter and as a tip softening means which allows said tip to flex and thereby prevents injury to a patient's vessel.

2. The improved catheter of claim 1 wherein catheter has a single lumen, and there is a single, elongated slit adjacent to the tip.

3. The improved catheter of claim 1 wherein the catheter has a single lumen and there are a plurality elongated slits adjacent to the tip which extend back along said elongated tube.

4. The improved catheter of claim 3 wherein said slits are spaced around the circumference of said catheter.

5. The improved catheter of claim 1 wherein material is removed from said at least one slit in order to improve fluid flow therethrough.

6. The improved catheter of claim 1 wherein said catheter has at least two lumens and said at least one slit is formed into at least one of said lumens.

* * * * *